United States Patent [19]

Kroenke et al.

[11] 4,406,839

[45] Sep. 27, 1983

[54] PROCESS FOR PREPARING ORGANIC SOLVENT SOLUBLE AMINE MOLYBDATES

[75] Inventors: William J. Kroenke; Angel J. Magistro, both of Brecksville, Ohio

[73] Assignee: The B. F. Goodrich Company, Akron, Ohio

[21] Appl. No.: 402,483

[22] Filed: Jul. 28, 1982

[51] Int. Cl.$^3$ ............................................. C07F 11/00
[52] U.S. Cl. ............................................. 260/429 R
[58] Field of Search ................................... 260/429 R

[56] References Cited

U.S. PATENT DOCUMENTS

| | | | |
|---|---|---|---|
| 4,164,473 | 8/1979 | Coupland et al. | 260/429 R X |
| 4,201,683 | 5/1980 | Brewster | 260/429 R X |
| 4,217,292 | 8/1980 | Kroenke | 260/429 R |
| 4,343,747 | 8/1982 | Ryu et al. | 260/429 R |

*Primary Examiner*—Helen M. S. Sneed
*Attorney, Agent, or Firm*—James R. Lindsay

[57] ABSTRACT

Amine molybdates are formed by reacting an amine with a molybdenum compound in a reaction mixture comprised of at least two immiscible liquid materials, one of which is an aqueous phase and another of which is a volatile organic solvent in which the amine molybdate to be formed is readily soluble. An inorganic or organic acid desirably is added to the reaction mixture.

8 Claims, No Drawings

PROCESS FOR PREPARING ORGANIC SOLVENT SOLUBLE AMINE MOLYBDATES

BACKGROUND OF THE INVENTION

Amine molybdates may be produced by reacting an amine or an amine salt with a molybdenum compound such as molybdenum trioxide ($MoO_3$), molybdic acid or a molybdenum salt in an acidic aqueous medium made acidic through the addition of a suitable acid such as an inorganic acid (exemplified by hydrochloric acid, nitric acid or sulfuric acid) or an organic acid containing 1 to 12 carbon atoms (exemplified by acetic acid, propionic acid, benzoic acid, and the like). The acidic mixture is refluxed, preferably while being stirred continuously, until the reaction is complete, usually for about ¼ to 16 hours. Amine molybdates also may be produced, as described in U.S. Pat. No. 4,217,292, by reacting essentially stoichiometric quantities of molydenum trioxide with an amine in an aqueous medium essentially free of acid and in which a water-soluble ammonium or monovalent metal or divalent metal or trivalent rare earth metal salt of an inorganic or organic acid is dissolved. The particular amine molybdate formed often depends upon which process is used to form the amine molybdate and the quantity of reactants present in the reaction mixture, as well as the reaction conditions.

Although many amine molybdates formed as a result of the aforementioned reactions exist as water-insoluble solid products that can be separated conveniently from the liquid phase of the reaction products by filtration, centrifugation or other suitable separation procedures, many of the amine molybdates are amorphous "solids" which have a sticky resinous consistency or exist as a viscous liquid material at room temperature (25° C.). When such amine molybdates are formed in an aqueous medium, they are difficult to separate from the aqueous phase, difficult to purify and difficult to handle. These amine molybdates, however, have been found to be soluble in many of the common organic solvents.

SUMMARY OF THE INVENTION

The present invention provides a process for making amine molybdates that comprises reacting an amine or an amine salt with a molybdenum compound (preferably in stoichiometric quantities) in a reaction medium comprised of two or more immiscible liquid materials, one of which is a volatile organic solvent in which the amine molybdate which is to be formed is readily soluble and another of which is an aqueous phase, (the term "volatile organic solvent", as used herein, shall mean any organic solvent for the amine molybdate that can be distilled at less than atmospheric pressure, i.e. 15 psi). Generally, the molybdenum reactant is dissolved in the aqueous phase and the amine or amine salt reactant is or becomes dissolved in the organic solvent phase of the reaction mixture. If required or desired, an inorganic or organic acid, that is soluble in the aqueous phase, may be added. The amine molybdate which forms becomes dissolved in the organic solvent phase in which it is soluble. The immiscible liquid phases in the reacted mixture are separated from each other by decantation, centrifugation or other appropriate separation procedures. Any undissolved solid reactant or reaction products present in the organic solvent phase that contains the dissolved amine molybdate product can be separated from such solvent phase, such as by filtration. The amine molybdate then can be recovered from the solvent phase, if desired, by evaporating the solvent, leaving the amine molybdate as the residue.

DETAILED DESCRIPTION OF THE INVENTION

In accordance with the present invention amine molybdates are prepared by reacting a molybdenum compound (such as molybdenum trioxide, molybdic acid or a molybdenum salt) with an amine or an amine salt in a reaction medium comprised of two or more immiscible liquid materials, one of which is a volatile organic solvent in which the amine molybdate to be formed is readily soluble and the other of which is an aqueous phase. Desirably, the amine or amine salt reactant is soluble in an organic liquid solvent phase of the reaction mixture which may be the same volatile organic solvent phase into which the amine molybdate reaction product dissolves or a different immiscible organic solvent material. Typically, a soluble molybdenum compound (molybdic acid or ammonium para- or dimolybdate, for example) is dissolved in the aqueous phase of the reaction mixture and the amine is dissolved in an organic solvent phase of the reaction mixture that is immiscible with the aqueous phase of the reaction mixture and the two liquid materials are added to the reaction vessel. An inorganic or organic acid may be added (and must in some cases be added). Sufficient liquid material is included in the reaction mixture to insure a mixture that has a consistency that enables the mixture to be easily stirred during the reaction. During the course of the reaction, interaction between the reactants is facilitated by the amine or amine salt which functions as a phase transfer catalyst to bring the reactants together at the water phase-organic solvent phase interface. Usually, the amine or amine salt and molybdate reactants are present in the reaction mixture in essentially stoichiometric quantities (based upon the molybdate product desired to be formed). The reaction may be run at room temperature, or at any temperature up to the reflux temperature of the mixture. The temperature influences the rate at which the reaction occurs and may even influence the particular composition of the product formed. To keep the reaction time relatively short, desirably, the reaction is run at a temperature between 75° C. to 110° C., while being stirred continuously. Reaction times of 0.08 to 72 hours are used, although the reactions usually are complete in about 0.25 to 16 hours. Preferably, the mixture then is cooled to about room temperature (25° C.) before separation of the immiscible phases of the mixture is attempted. The immiscible liquid phases of the mixture are separated from each other by decantation, centrifugation or other appropriate separation procedures. The amine molybdate formed during the reaction remains dissolved in the organic solvent phase during the separation of the immiscible liquid phases of the mixture. The recovered organic solvent phase in which the amine molybdate is dissolved then desirably is washed with water or an immiscible organic liquid material to remove impurities from the recovered component. Desirably, any moisture that might have become entrapped in the organic solvent component (that contains the amine molybdate) is removed (for example, by "drying" over a desiccant, such as calcium hydride, or over molecular sieves). Any solid impurities in the component can be removed by filtration or centrifugation, or other suitable procedure. The amine molybdate dissolved in the organic solvent then can be recovered by evaporating the organic solvent from the amine molybdate. Evaporation of the organic solvent from the amine molybdate can be accelerated by heating the solution.

Amines suitable for preparing the amine molybdates using the process of this invention are any amine or amine salt that will react with molybdenum trioxide, molybdic acid or a molybdenum salt to form an amine molybdate that is soluble in an organic solvent that forms an immiscible liquid phase with water. Suitable amines include polymeric amines as well as simple amines. The simple amines may contain from 1 to 75 carbon atoms and from 1 to 10 primary, secondary or tertiary amine groups or a mixture thereof, more preferably from 1 to 6 groups. Simple amines include aliphatic amines (such as ethylamine, ethylenediamine, 1,2-propanediamine, 1,3-propanediamine, 1,4-butanediamine, 2-methyl-1,2-propanediamine, 1,5-pentanediamine, 1,6-hexanediamine, 1,7-heptanediamine, 1,8-octanediamine, 1,10-decanediamine, 1,12-dodecanediamine, diethylenetriamine, triethylenetetramine, tetraethylenepentamine, bis(hexamethylene)triamine, and the like), alicyclic amines (such as 1,2-diaminocyclohexane, 1,8-p-methanediamine, and the like), aromatic amines (such as aniline, N,N-dimethylaniline, and the like), and heterocyclic amines (such as melamine and substituted melamines, ammeline, pyridine, piperazine, hexamethylenetetramine, 2,2,4-trimethyl decahydroquinoline, and N-(aminoalkyl)-piperazines wherein each alkyl group contains from 1 to 12 carbon atoms such as N-(2-aminoethyl)-piperazine, and the like). Examples of suitable polymeric amines include polyethyleneimine, polyvinylpyridine, and polyvinylpyrrolidine.

Illustrative amine salts that may be used for preparing amine molybdates using the process of this invention are tetrapentylammonium bromide, didodecyldimethylammonium bromide, dioctadecylammonium bromide and methyltricaprylammonium chloride.

The volatile organic solvent component of the reaction mixture into which the amine molybdate formed during the reaction dissolves may be any volatile organic solvent in which the amine molybdate formed is readily soluble. Typical volatile organic solvents which dissolve many amine molybdates include aliphatic solvents (including alcohols), such as pentane, hexane, heptane, octane, decane, petroleum ether, kerosene, methanol, ethanol, isopropanol, and the like; aromatic solvents, such as benzene, toluene, naphthalene, xylene, cumene, mesitylene, and the like; chlorinated solvents, such as dichloromethane, 1,1-dichloroethane, 1,2-dichloroethane, tetrachloroethane, chlorobenzene, polychlorobenzenes, and the like; and ketones, such as acetone, 2-butanone, 3,3-dimethylbutanone, and the like.

The process of the present invention is more fully illustrated by the following examples.

EXAMPLE I 13.02 grams of ammonium dimolybdate was dissolved in 400 milliliters of water. The solution was added to a 3-liter round-bottom flask equipped with a water-cooled reflux condenser and a mechanical stirrer. 250 additional milliliters of water were added to the flask. 7.60 grams of a 37 percent hydrochloric acid solution were mixed with 40 milliliters of water and then added to the flask. 60 additional milliliters of water were added to the flask, 20 grams of tridodecylamine were dissolved in 200 milliliters of cyclohexane and then added to the flask. 500 additional milliliters of cyclohexane then were added to the flask. The mixture was heated to reflux and refluxed for 15 minutes while being stirred continuously. The mixture then was allowed to cool to room temperature (about 25° C.) and was transferred to a separatory funnel. Upon standing, the mixture separated into a clear aqueous phase in the bottom of the funnel and a bright yellow-green cyclohexane phase floating on top of the aqueous phase. The two phases were separated from each other. The cyclohexane phase was washed three times with separate washes consisting of 150 milliliters of water, the wash water being funneled off after each washing, and then was dried over calcium hydride for 66 hours. The cyclohexane was evaporated from a sample of the cyclohexane phase. Infrared analysis identified the residue (a yellow-green sticky mass) to be tridodecylammonium beta-octamolybdate.

EXAMPLE II 6.00 grams of tri(tridecyl)amine were dissolved in 80 milliliters of methylene chloride and added to a 1000 milliliter round-bottom flask equipped with a water-cooled reflux condenser and a mechanical stirrer. 126 additional milliliters of methylene chloride were added to the flask. 3.58 grams of ammonium dimolybdate were dissolved in 160 milliliters of water. 2.07 grams of 37 percent hydrochloric acid were added to 20 milliliters of water. The aqueous hydrochloric acid solution was combined with the ammonium dimolybdate solution. The combined aqueous solutions were added to the round-bottom flask. 26 milliliters of additional water were added to the flask. The mixture in the flask was heated to reflux and refluxed while being stirred continuously for one hour. As the mixture was heated, the cloudy white mixture changed to light green in color. The contents in the flask were cooled to room temperature (about 25° C.) and added to a separatory funnel and the two immiscible phases were separated, one phase being an aqueous phase and the other being the methylene chloride phase. The methylene chloride phase was washed three times with water, separating the methylene chloride phase from the water phase after each washing. The reaction product which remained dissolved in the methylene chloride phase was identified by infrared analysis to be a mixture predominately of tri(tridecyl)ammonium beta-octamolybdate with a small amount of tri(tridecyl)ammonium hexamolybdate.

EXAMPLE III 3.91 grams of ammonium dimolybdate were dissolved in 180 milliliters of water and were added to a 1000 milliliter round-bottom flask equipped with a water-cooled reflux condenser and a mechanical stirrer. 2.27 grams of 37 percent hydrochloric acid were added to 45 milliliters of water and added to the flask. 6.00 grams of tridodecylamine were dissolved in 225 milliliters of methylene chloride and were added to the flask. The reaction mixture was heated to reflux and refluxed for 1 hour while being stirred continuously. The contents of the flask were cooled to room temperature (about 25° C.) and were transferred to a 1000 milliliter separatory funnel. The aqueous phase was separated from the methylene chloride phase. The methylene chloride phase was washed three times with separate washes consisting of 25 milliliters of water, the wash water being funneled off after each washing. The washed methylene chloride phase then was dried. The methylene chloride was evaporated from the methylene chloride phase leaving a light yellow colored sticky residue. Infrared analysis identified the residue to be tridodecylammonium beta-octamolybdate.

EXAMPLE IV 1.30 grams of ammonium dimolybdate were dissolved in 50 milliliters of water and added to a 250 milliliter round-bottom flask equipped with a water-cooled reflux condenser and a machanical stirrer. 0.75 gram of 37 percent hydrochloric acid was added to 10 milliliters of water and added to the flask. 15 additional milliliters of water were added to the flask. 2.00 grams of tridodecylamine were dissolved in 25 milliliters of toluene and added to the flask. 50 additional milliliters of toluene then were added to the flask. The reaction mixture in the flask was heated to reflux and refluxed for 20 minutes while being stirred continuously. The contents of the flask were cooled to room temperature (about 25° C.) and were transferred to a 500 milliliter separatory funnel. The aqueous phase was separated from the toluene phase. The toluene phase was washed three times with separate washes consisting of 20 milliliters of water, the wash water being funneled off after each washing. The toluene phase was dried over molecular sieves for 16 hours. The toluene was evaporated from the toluene phase leaving a light yellow-green colored sticky residue. Infrared analysis identified the residue to be a mixture comprised predominantly of tridodecylammonium beta-octamolybdate with a minor amount of tridodecylammonium alpha-octamolybdate.

EXAMPLE V

Example IV was repeated except that cyclohexene was used in place of toluene. Infrared analysis identified the residue to be a mixture comprised predominantly of tridodecylammonium beta-octamolybdate with a minor amount of tridodecylammonium alpha-octamolybdate.

EXAMPLE VI

Example IV was repeated except that cyclohexane was used in place of toluene and except that the reaction took place at room temperature (about 25° C.) during a 2-hour reaction time. Infrared analysis identified the residue to be a mixture of tridodecylammonium alpha-octamolybdate, tridodecylammonium beta-octamolybdate and tridodecylammonium paramolybdate.

EXAMPLE VII 1.10 grams of molybdenum trioxide and 75 milliliters of water were added to a 250 milliliter round-bottom flask equipped with a water-cooled reflux condenser and a mechanical stirrer. 2.00 grams of tridodecylamine were dissolved in 75 milliliters of cyclohexane and added to the flask. The reaction mixture in the flask was heated to reflux and refluxed for two hours while being stirred continuously. The contents of the flask were cooled to room temperature (about 25° C.) and were transferred to a 1000 milliliter separatory funnel. The aqueous phase was separated from the cyclohexane phase. The cyclohexane phase was washed three times with separate washes consisting of 20 milliliters of water, the wash water being funneled off after each washing. The cyclohexane phase was dried over molecular sieves for 16 hours. The cyclohexane was evaporated from the cyclohexane phase leaving a light green residue. Infrared analysis identified the residue to be a mixture of tridodecylammonium alpha-octamolybdate, tridodecylammonium beta-octamolybdate and tridodecylammonium paramolybdate.

Amine molybdates have been found to be effective smoke retardant additives for vinyl chloride polymer and vinylidene chloride polymer compositions. Solid amine molybdates can be added to the vinyl chloride polymer or vinylidene chloride polymer by milling the solid amine molybdate in particulate form with the vinyl chloride polymer resin or vinylidene chloride resin. However, amine molybdates that are soluble in a volatile organic solvent can be dissolved in the organic solvent and mixed with the vinyl chloride polymer resin or vinylidene chloride polymer resin in particulate form to distribute the amine molybdate evenly throughout the resin. The volatile organic solvent is evaporated from the resin leaving the amine molybdate evenly dispersed upon the surfaces of the resin particles, or, if a solvent is chosen which swells the resin, amine molybdate will be dissolved in the resin particles. This manner of combining the amine molybdate with the vinyl chloride polymer or vinylidene chloride polymer is of particular significance when the amine molybdate is not a solid material, but, instead, is an amorphous tacky material or viscous liquid material that is difficult to evenly disperse with the resin in its undissolved state. The smoke retardant vinyl chloride polymer or vinylidene chloride polymer compositions are useful wherever smoke reduction is a desirable property, such as in carpeting, house siding, plastic components for aircraft and passenger car interiors, and the like.

We claim:

1. A process for making an amine molybdate comprising combining together in a reaction vessel an amine or amine salt, a molybdate or molybdic acid or molybdenum trioxide, and at least two immiscible liquid materials, one of said immiscible liquid materials being an aqueous phase and one of said immiscible liquid materials being a volatile organic solvent phase in which the amine molybdate formed by the reaction of the said amine or amine salt and said molybdenum compound is soluble, continuously stirring the mixture in said reaction vessel for 0.08 to 72 hours thereby causing the said amine or amine salt and molybdenum compound to react together and form said amine molybdate as a solute in said volatile organic solvent phase, and separating said volatile organic solvent phase with said amine molybdate dissolved therein from other immiscible liquid phases of said mixture.

2. The process of claim 1 wherein an inorganic or organic acid is added to the reaction mixture.

3. The process of claim 1 wherein the reaction mixture is heated to reflux and refluxed with continuous stirring of the said reaction mixture during the said reaction period.

4. The process of claim 2 wherein the said molybdenum compound is molybdenum trioxide.

5. The process of claim 2 wherein the said molybdenum compound is ammonium dimolybdate.

6. The process of claim 1 wherein the said separated volatile organic solvent phase with said amine molybdate dissolved therein is filtered to remove particles of solid undissolved material therefrom.

7. The process of claim 6 wherein the said volatile organic solvent is evaporated from the said separated and filtered volatile organic solvent phase to separate said amine molybdate from the said volatile organic solvent.

8. The process of claim 1 wherein the said mixture is reacted at a temperature between 75° to 110° C.

* * * * *